United States Patent [19]

Hill

[11] Patent Number: 5,399,712
[45] Date of Patent: Mar. 21, 1995

[54] PROCESS FOR THE PREPARATION OF 2-SUBSTITUTED AND 2,3-DISUBSTITUTED MALEIMIDES

[75] Inventor: Christopher H. Hill, Knebworth, England

[73] Assignee: Hoffmann-La Roche Inc., Nutley, N.J.

[21] Appl. No.: 971,370

[22] Filed: Nov. 4, 1992

[30] Foreign Application Priority Data

Nov. 4, 1991 [GB] United Kingdom ............. 9123396

[51] Int. Cl.[6] ................ C07D 403/14; C07D 403/04; C07D 207/456; C07D 409/04
[52] U.S. Cl. .................... 578/455; 548/466; 548/544; 548/552; 548/527
[58] Field of Search ............ 548/552, 544, 455, 466, 548/527

[56] References Cited

U.S. PATENT DOCUMENTS

| | | | |
|---|---|---|---|
| 4,332,822 | 6/1982 | Ward | 548/544 |
| 4,886,908 | 12/1989 | Haeusler | 548/544 |
| 4,962,204 | 10/1990 | Wambach | 548/543 |
| 5,057,614 | 10/1991 | Davis et al. | 548/466 |

FOREIGN PATENT DOCUMENTS

| | | |
|---|---|---|
| 9050033 | 2/1990 | Australia . |
| 384349 | 7/1991 | European Pat. Off. . |
| 470490 | 7/1991 | European Pat. Off. . |

*Primary Examiner*—David B. Springer
*Attorney, Agent, or Firm*—George M. Gould; George W. Johnston

[57] ABSTRACT

The invention relates to a process for the manufacture of substituted maleimides of the formula

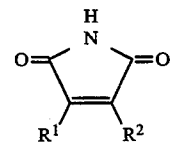

wherein $R^1$ is alkyl, aryl or heteroaryl and $R^2$ is hydrogen, alkyl, alkoxycarbonyl, aryl or heteroaryl, by reacting an activated glyoxylate of the formula

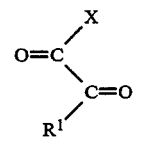

wherein $R^1$ has the above significance and X is a leaving atom or group,
with an imidate of the formula

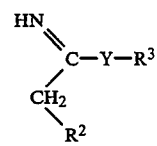

wherein $R^2$ has the above significance, $R^3$ is alkyl, aryl or trialkylsilyl and Y is oxygen or sulfur, in the presence of a base and, after treating the resulting reaction product obtained in which $R^2$ is hydrogen or alkyl with a strong base, hydrolyzing and dehydrating the resulting hydroxy-pyrrolinone of the formula

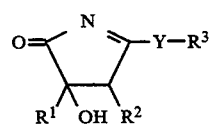

wherein $R^1$, $R^2$, $R^3$ and Y have the above significance. logically active, for example as protein kinase C inhibitors and which a useful, for example, in the treatment and prophylaxis of inflammatory, immunological, bronchopulmonary and cardiovascular disorders, or as antiproliferative agents useful, for example, in the treatment of immune diseases and allergic disorders.

10 Claims, No Drawings

PROCESS FOR THE PREPARATION OF 2-SUBSTITUTED AND 2,3-DISUBSTITUTED MALEIMIDES

BRIEF SUMMARY OF THE INVENTION

The invention relates to a process for the preparation of 2-substituted and 2,3-disubstituted maleimides of the formula

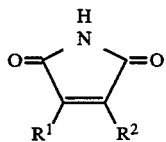

wherein $R^1$ is alkyl, aryl or heteroaryl, and $R^2$ is hydrogen, alkyl, alkoxycarbonyl, cycloalkyl, aryl or heteroaryl.

The substituted maleimides of formula I hereinbefore have valuable pharmacological properties. For example, they are protein kinase C (PKC) inhibitors as described, for example, in U.S. Pat. No. 5057614, EPA 0384349 and EPA 0470490 or antiproliferative agents as described, for example, in DE 4005970.

DETAILED DESCRIPTION OF THE INVENTION

The invention relates to a process for the preparation of substituted maleimides.

More particularly, the invention relates to a process for the preparation of 2-substituted and 2,3-disubstituted maleimides of the formula

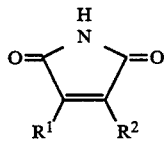

wherein $R^1$ is alkyl, aryl or heteroaryl, and $R^2$ is hydrogen, alkyl, alkoxycarbonyl, cycloalkyl, aryl or heteroaryl.

The substituted maleimides of formula I hereinbefore have valuable pharmacological properties. For example, they are protein kinase C (PKC) inhibitors as described, for example, in U.S. Pat. No. 5057614, EPA 0384349 and EPA 0470490 or antiproliferative agents as described, for example, in DE 4005970.

As used herein, the term 'alkyl' denotes a straight-chain or branched-chain alkyl group which preferably contains a maximum of 8 carbon atoms, for example, methyl, ethyl, propyl, isopropyl, butyl, isobutyl, tert.butyl, pentyl, hexyl, heptyl and the like. The term 'alkoxycarbonyl' describes a straight-chain or branched-chain alkoxy- carbonyl group which preferably contains a maximum of 8 carbon atoms in the alkoxy group, for example, methoxycarbonyl, ethoxycarbonyl, isopropoxycarbonyl and the like. The term 'cycloalkyl' denotes a cycloalkyl group which preferably contains from 3 to 8 carbon atoms and which can be optionally substituted, for example, cyclopropyl, cyclobutyl, cyclopentyl, cyclohexyl and the like. The term 'aryl' denotes an optionally substituted monocyclic, bicyclic or polycyclic aromatic ring, for example, phenyl, naphthyl, anthryl, phenanthryl and the like. The term 'heteroaryl' denotes an optionally substituted monocyclic, bicyclic or poly- cyclic aromatic ring in which one or more carbon atoms have been replaced by one or more nitrogen, oxygen and/or sulfur atoms, for example, pyridyl, thienyl, indolyl, benzothiophenyl and the like.

According to the invention the substituted maleimides of formula I hereinbefore are prepared by reacting an activated glyoxylate of the formula

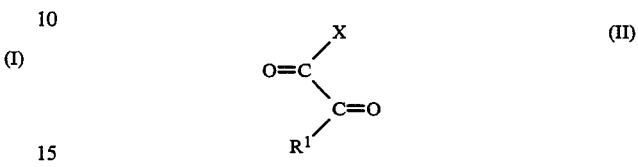

wherein $R^1$ has the significance given earlier and X is a leaving atom or group, with an imidate of the formula

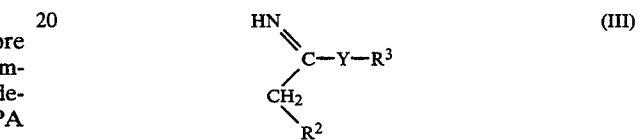

wherein $R^2$ has the significance given earlier, $R^3$ is alkyl, aryl or trialkylsilyl and Y is oxygen or sulfur, in the presence of a base and, after treating the resulting reaction product in which $R^2$ is hydrogen or alkyl with a strong base, hydrolyzing and dehydrating the resulting hydroxy-pyrrolinone of the formula

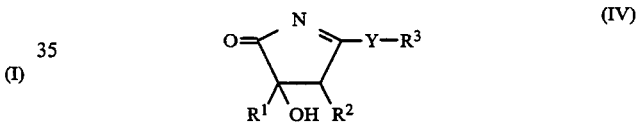

wherein $R^1$, $R^2$, R3 and Y have the significance given earlier.

The leaving atom or group denoted by X in an activated glyoxylate of formula II can be, for example, a halogen atom such as chlorine, an alkoxycarbonyloxy group, such as methoxycarbonyloxy, ethoxycarbonyloxy, isopropoxycarbonyloxy and the like, the pentafluoro- phenoxy group, or the like. In a preferred embodiment, X is a halogen atom, especially chlorine.

The reaction of an activated glyoxylate of formula II with an imidate of formula III is conveniently carried out in an organic solvent which is inert under the conditions of the reaction. Suitable bases are, for example, tertiary amines, such as triethylamine, diisopropylethylamine, 4-dimethylaminopyridine, N-ethylmorpholine, 1,4-diazabicyclo[2,2,2]octane and the like, pyridine and the like. Suitable solvents are, for example, halogenated aliphatic hydrocarbons, such as dichloromethane, chloroform and the like, optionally halogenated aromatic hydrocarbons, such as, benzene, toluene, chlorobenzene and the like, open-chain and cyclic ethers, such as, dimethoxyethane, tert.butyl methyl ether, tetrahydrofuran and the like, formamides, such as, dimethylformamide and the like, esters, such as ethyl acetate and the like and nitriles, such as, acetonitrile and the like. The reaction is preferably carried out at about 0° C. to about 40° C., especially at about room temperature.

When a substituted glyoxylate of formula II in which $R^2$ is hydrogen or alkyl is used, the reaction product obtained must be treated with a strong base. Especially suitable strong bases are alkali metal alkoxides, particularly potassium tert.butoxide.

The hydrolysis and dehydration of a hydroxy-pyrrolinone of formula IV to give a substituted maleimide of formula I is expediently carried out by treatment with, for example, a mineral acid, such as, hydrochloric acid, sulfuric acid and the like, or an organic acid, such as, methanesulfonic acid, p-toluenesutfonic acid and the like, or by treatment with an acylating reagent, for example, trifluoroacetic anhydride, and a suitable base, such as, pyridine, conveniently at about room temperature. The hydroxy-pyrrolinone of formula IV is preferably hydrolyzed and dehydrated in situ, that is the process is preferably carried out as a so-called "one-pot" process.

The activated glyoxylate starting materials of formula II are known compounds or analogues of known compounds which can be prepared in analogy to the known compounds or as described in the following Examples or in analogy thereto.

The imidate starting materials of formula III, insofar as they are not known compounds or analogues of known compounds, can be prepared by reacting a nitrile of the formula

$$R^2-CH_2-CN \quad (V)$$

wherein $R^2$ has the significance given earlier, with a compound of the formula

$$H-Y-R^3 \quad (VI)$$

wherein $R^3$ has the significance given earlier. The reaction is carried out in a known manner, for example, in the presence of hydrogen chloride.

Alternatively, imidate starting materials of formula III in which $R^3$ is trialkylsilyl and Y is oxygen-can be prepared by reacting an amide of the formula

$$R^2-CH_2-CONH_2 \quad (VII)$$

wherein $R^2$ has the significance given earlier with a halotrialkylsilane, for example, chlorotrimethylsilane, in the presence of triethylamine. The reaction is carried out in a known manner, for example in a solvent which is inert under the reaction conditions, for example, a halogenated hydrocarbon such as dichloro- methane and the like, and at about room temperature.

Preferred activated glyoxylate starting materials of formula II are those in which $R^1$ is optionally substituted phenyl, naphthyl, thienyl, benzothiophenyl or indolyl especially a 3-indolyl group of the formula

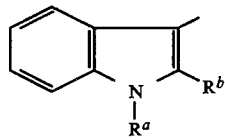

(a)

wherein $R^a$ is alkyl, particularly methyl, or alkanoyl, particularly acetyl, and $R^b$ is hydrogen or alkyl, particularly methyl, or $R^a$ and $R^b$ taken together are a tetramethylene group optionally substituted by acyloxyalkyl, particularly acetoxymethyl.

Preferred imidate starting materials of formula III are those in which $R^2$ is optionally substituted indolyl, especially 3-indolyl or 1-alkyl-3-indolyl, particularly 1-methyl-3-indolyl, and $R^3$ is secondary alkyl, especially isopropyl.

As mentioned earlier, the substituted maleimides of formula I are, for example, protein kinase C inhibitors, which can be used, for example, in the treatment and prophylaxis of inflammatory, immunological, bronchopulmonary land cardiovascular disorders, or antiproliferative agents, which can be used, for example, in the treatment of immune diseases and allergic disorders. The present invention enables these substituted maleimides to be prepared in good yields and purity starting from readily accessible starting materials.

The following Examples further illustrate the invention.

EXAMPLE 1

A solution of 235 mg (1 mmol) of 1,2-dimethylindole-3-glyoxylyl chloride in 20 ml of dry dichloromethane was added dropwise to a solution of 266 mg (1 mmol) of isopropyl 1-methyl-3-indoleacetimidate hydrochloride and 404 mg (4 mmol) of triethylamine in 20 ml of dry dichloromethane containing 4Å molecular sieves. On completion of the addition, the mixture was stirred at room temperature under nitrogen for 18 hours. Then, 950 mg (5 mmol) of p-toluenesulfonic acid were added and stirring was continued for 1 hour. The mixture was filtered. The filtrate was evaporated to dryness and the residue was purified by flash chromatography on silica gel using dichloromethane/ethyl acetate (8:1) for the elution. There were obtained 257 mg (70%) of 3-(1,2-dimethyl-3-indolyl)-4-(1-methyl-3-indolyl)-1H-pyrrole-2,5-dione in the form of a red solid of melting point >290° C.

The isopropyl 1-methyl-3-indoleacetimidate hydrochloride used as the starting material was prepared as follows:

Hydrogen chloride was bubbled through a stirred solution of 7.5 g (44 mmol) of 1-methylindole-3-acetonitrile in 100ml of dry isopropanol at room temperature. After 4 hours, the solvent was removed under reduced pressure and the residue was triturated with diethyl ether to give 5.17 g (44%) of isopropyl 1-methyl-3-indoleacetimidate hydrochloride as a white solid of melting point 133° C.

Example 2

A stirred solution of 10 g (41 mmol) of (S)-8-(acetoxymethyl)-6,7,8,9-tetrahydropyrido[1,2-a]indole in 100ml of dichloromethane was treated dropwise at 0° C. with 4.3 ml (49 mmol) of oxalyl chloride. After 5 minutes, the solvent was removed by evaporation under reduced pressure. The residue was suspended in 150 ml of toluene and treated with 9.5 g (41 mmol) of isopropyl 1-methyl-3-indoleacetimidate hydrochloride (prepared as described in Example 1). The stirred suspension was cooled to 0° C. and treated dropwise with 23 ml (166 mmol) of triethylamine. After stirring for 18 hours at room temperature under nitrogen, the thick suspension was partitioned between dichloromethane, toluene and 0.5M hydrochloric acid. The organic extracts were dried over sodium sulfate, filtered and treated with a suspension of 15.6 g (82 mmol) of p-toluene sulfonic acid in 100 ml of toluene. The mixture was stirred at room temperature for 2.5 hours, washed with water, saturated sodium bicarbonate solution and brine, dried over sodium sulfate and evaporated to give a brown solid. Trituration with diethyl ether gave 13.73 g 72% of (S)-3-[8-(acetoxymethyl)-6,7,8,9tetrahydropyrido[1,2-a ]indol- 10-yl ]-4-(1-methyl-3-indolyl)-1H-pyrrole-2,5-dione. A sample was crystallized from dichloromethane/methanol to give an orange solid of melting point 238°-241° C.

The (S)-8-(acetoxymethyl)-6,7,8,9-tetrahydropyrido[1,2a]indole used as the starting material was prepared as follows:

A mixture of 4.47 g (20.8 mmol) of 6,7,8,9-tetrahydropyrido[1,2-a]indole-8-carboxylic acid and 3.9 g (25 mmol) of l-menthol in 100 ml of dichloromethane was treated with 0.25 g (2.05 mmol)of 4-dimethylaminopyridine and cooled in ice. Then, 6.08 g (22.9 mmol) of dicyclohexylcarbodiimide in 20 ml of dichloromethane were added dropwise over 10 minutes. After 0.5 hour, the suspension was filtered through a pad of diatomaceous earth and the filtrate was evaporated. Flash chromatography (diethyl ether/hexane, 1:5) gave 6.09 g (83%) of mixed diastereoisomers as an oil. The isomers were separated either by flash chromatography on silica gel using diethyl ether/hexane (1:9) for the elution or by fractional crystallization from isopropanol. Menthyl 6,7,8,9-tetrahydropyrido[1,2-a]indole-8(S)-carboxylate melted at 117°-118° C. and had the rotation $[\alpha]_{589}{}^{20} = -76.2°$ (c=% in chloroform). The corresponding (R) isomer melted at 87°-89° C. and had the rotation $[\alpha]_{589}{}^{20} = -22.8°$ (c=1% in chloroform).

A solution of 0.8 g (2.27 mmol) of 1-menthyl 6,7,8,9tetrahydropyrido[1,2-a]indole-8(S)-carboxylate in 15 ml of dry tetrahydrofuran was treated dropwise under a nitrogen atmosphere with 2 ml (2 mmol) of 1M lithium aluminum hydride. After 10 minutes, the mixture was cooled in ice, treated successively with 5 ml of ethyl acetate and 30 ml of water and acidified with 1M hydrochloric acid. The mixture was extracted three times with diethyl ether and the combined extracts were dried over sodium sulfate and evaporated. Flash chromatography on silica gel using ethyl acetate/hexane (1:1) for the elution gave (S)-8-(hydroxymethyl)-6,7,8,9-tetrahydropyrido[1,2-a]indole as a white solid which was dissolved in 5 ml of dichloromethane. Then, 0.43 g (4.21 mmol) of acetic anhydride and 0.9 ml (6.5 mmol) of triethylamine were added and the solution was left to stand for 17 hours. The solvent was evaporated. The residue was partitioned between 5% aqueous sodium bicarbonate solution and diethyl ether. The organic phase was dried over sodium sulfate and evaporated. The residue was crystallized from aqueous ethanol to give 0.518 g (94%) of (S)-8-(acetoxymethyl)-6,7,8,9-tetrahydropyrido[1,2-a]indole as a white solid of melting point 63°-64° C.; $[\alpha]_{589}{}^{20} = 43.7°$ (c=1% in chloroform).

Example 3

In a manner analogous to that described in Example 1, from 222 mg (1 mmol) of 1-methylindole-3-glyoxylyl chloride and 213 mg (1 mmol) of isopropyl phenylacetamidate hydrochloride, there were obtained 185 mg (61%) of 3-(1-methyl-3-indolyl)-4-phenyl-1H-pyrrole-2,5-dione in the form of an orange solid of melting point 230°-232° C.

Example 4

In a manner analogous to that described in Example 1, from 222 mg (1 mmol) of 1-methylindole-3-glyoxylyl chloride and 263 mg (1 mmol) of isopropyl 2-naphthaleneacetimidate hydrochloride, there were obtained 174 mg (49%) of 3-(1-methyl-3-indolyl)-4-(2-naphthyl)-1H-pyrrole -2,5-dione in the form of an orange solid of melting point 269°-271° C.

The isopropyl 2-naphthaleneacetimidate hydrochloride used as the starting material was prepared in a manner analogous to that described in Example 1 from 2-naphthylacetonitrile. It was obtained in the form of a white solid of melting point 180°-184° C.

Example 5

In a manner analogous to that described in Example 1, from 222 mg (1 mmol) of 1-methylindole-3-glyoxylyl chloride and 269 mg (1 mmol) of isopropyl 3-benzothiopheneacetimidate hydrochloride, there were obtained 196 mg (55%) of 3-(1-benzothiophen-3-yl) -4-(1-methyl-3-indolyl)-1H-pyrrole-2,5-dione as an orange solid of melting point 238°-241° C.

The isopropyl 3-benzothiopheneacetimidate hydrochloride used as the starting material was prepared as follows:

In a manner analogous to that described in Example 1, from benzothiophene-3-acetonitrile, there was obtained isopropyl 3-benzothiopheneacetimidate hydrochloride as a cream colored solid of melting point 93°-95° C.

Example 6

In a manner analogous to that described in Example 1, from 222 mg (1 mmol) of 1-methylindole-3-glyoxylyl chloride and 294 mg (1 mmol) of isopropyl 1-acetyl-3-indoleacetimidate hydrochloride, there were obtained 184 mg (48%) of 3-(1-acetyl-3-indolyl) -4-( 1-methyl-3-indolyl)-1H-pyrrole-2,5-dione in the form of a red solid of melting point 252°-253° C.

The isopropyl 1-acetyl-3-indoleacetimidate hydrochloride used as the starting material was prepared as follows:

In a manner analogous to that described in Example 1, from 1-acetylindole-3-acetonitrile, there was obtained isopropyl 1-acetyl-3-indoleacetimidate hydrochloride in the form of a white solid of melting point 122°-125° C.

Example 7

In a manner analogous to that described in Example 1, from 222 mg (1 mmol) of 1-methylindole-3-glyoxylyl chloride and 225 mg (1 mmol) of isopropyl 3-thiopheneacetimidate hydrochloride, there were obtained 105 mg (58%) of 3-(1-methyl-3-indolyl)-4-(3-thienyl) -1H-pyrrole-2,5-dione in the form of an orange colored solid of melting point 225°-227° C.

The isopropyl 3-thiopheneacetimidate hydrochloride used as the starting material was prepared as follows:

In a manner analogous to that described in Example 1, from 3-thiopheneacetonitrile, there was obtained isopropyl 3-thiopheneacetimidate hydrochloride in the form of a beige solid of melting point 118°-119° C.

Example 8

In a manner analogous to that described in Example 1, from 222 mg (1 mmol) of 1-methylindole-3-glyoxylyl chloride and 225 mg (1 mmol) of isopropyl 3-imino-3-isopropoxypropionate hydrochloride, there were obtained 71 mg (23%) of 3-(isopropoxycarbonyl) -4-(1-methyl-3-indolyl)-1H-pyrrole-2,5-dione in the form of an orange colored solid of melting point 199°-202° C.

The isopropyl 3-imino-3-isopropoxypropionate hydrochloride used as the starting material was prepared as follows:

In a manner analogous to that described in Example 1, from isopropyl 2-cyanoacetate, there was obtained isopropyl 3-imino-3-isopropoxypropionate hydrochloride in the form of a beige solid of melting point 73°–75° C.

Example 9

165 mg (1.38 mmol) of oxalyl chloride were added to a stirred solution of 300 mg (1.24 mmol) of 8-acetoxymethyl-6,7,8,9-tetrahydropyrido[1,2-a]indole in 50 ml of dichloromethane at 0° C. The resulting solution was stirred for 15 minutes and the solvent was removed by evaporation. The residue was dissolved in 30 ml of toluene and added dropwise to a stirred solution of 496 mg (4.96 mmol) of triethylamine and mg (1.31 mmol) of isopropyl 3-indoleacetimidate hydrochloride in 20 ml of toluene. After 18 hours, 1.16 g (6.2 mmol) of p-toluenesulfonic acid were added and stirring was continued for 1 hour. The mixture was then partitioned between dichloromethane and water. The organic phase was dried over sodium sulfate and evaporated to dryness. The residue was purified by flash chromatography on silica gel using ethyl acetate/petroleum ether (1:1) for the elution to give 170 mg (38%) of 3-[8-(acetoxymethyl)-6,7,8,9-tetrahydropyrido[1,2-a]indol-10-yl]-4-[3-indolyl)-1H-pyrrole-2,5-dione in the form of an orange colored solid of melting point 264°–265° C.

The isopropyl 3-indoleacetimidate hydrochloride used as the starting material was prepared as follows:

In a manner analogous to that described in-Example 1, from indole-3-acetonitrile, there was obtained isopropyl 3-indoleacetimidate hydrochloride as a beige solid of melting point 132°–134° C.

Example 10

A stirred solution of 406 mg (2 mmol) of 1-methyl-3-indolylglyoxylic acid in 20ml of dichloromethane was treated with 202 mg (2 mmol) of triethylamine and 273 mg (2 mmol) of isobutyl chloroformate. After 0.5 hour, the solution was added dropwise to a stirred solution of 533 mg (2 mmol) of isopropyl 1-methyl-3-indoleacetimidate hydrochloride and 808 mg (8 mmol) of triethylamine in 50 ml of dichloromethane. The solution obtained was heated to reflux under nitrogen for 18 hours, cooled and treated with 1.9 g (10 mmol) of p-toluenesulfonic acid. After 1 hour, the solvent was removed under reduced pressure and the residue was purified by flash chromatography on silica gel using dichloromethane/ethyl acetate (8:1) for the elution to give 107 mg( 30% ) of 3,4-bis-( 1 -methyl-3-indolyl)-1H-pyrrole-2,5-dione in the form of an orange colored solid of melting point >310° C.

Example 11

A stirred solution of 1.0 g (7.6 mmol) of 1-methylindole in 25 ml of diethyl ether was treated at 0° C. under a nitrogen atmosphere with 1.81 g (8.4 mmol) of oxalyl bromide. After 1 hour, the brown-red solid was removed by filtration and dried to give 1.2 g of 1-methylindole-3-glyoxylyl bromide. A solution of 266 mg (1 mmol) of this bromide in 25 ml of dichloromethane was added dropwise to a stirred solution of 266 mg (1 mmol) of isopropyl 1-methyl-3-indoleacetimidate hydrochloride and 404 mg (4 mmol) of triethylamine in 25 ml of dry dichloromethane. After 18 hours 950 mg (5 mmol) of p-toluenesulphonic acid were added and the mixture was stirred for 1 hour. The solvent was removed under reduced pressure and the residue was purified on silica gel using dichloromethane/ethyl acetate (8:1) for the elution to give 136 mg (38%) of 3,4-bis-(1-methyl-3-indolyl) -1H-pyrrole-2,5-dione as a red solid of melting point >31° C.

Example 12

In a manner analogous to that described in Example 1, from 222 mg (1 mmol) of 1-methylindole-3-glyoxylyl chloride and 283 mg (1 mmol) of isopropyl 1-methyl-3-indolethioacetimidate hydrochloride, there were obtained 246 mg (69%) of 3,4-bis(1-methyl-3-indolyl) -1H-pyrrole-2,5-dione as a red solid of melting point >300° C.

The isopropyl 1-methyl-3-indolethioacetimidate hydrochloride used as the starting material was prepared as follows:

Hydrogen chloride was bubbled through a stirred solution of 3 g (17.6 mmol) of 1-methylindole-3-acetonitrile and 6.7 g (88 mmol) of 2-propanethiol in 70 ml of dry diethyl ether for 2 hours. The mixture was left to stand for 3 days and then diluted with diethyl ether. The ether was decanted and the residual gum was triturated with diethyl ether to give 3.76 g (87%) of isopropyl 1-methyl-3-indolethioacetimidate hydrochloride in the form of a grey solid of melting point 150° C.

Example 13

In a manner analogous to that described in Example 1, from 222 mg (1 mmol) of 1-methylindole-3-glyoxylyl chloride and 301 mg (1 mmol) of phenyl 1-methyl-3-indoleacetimidate hydrochloride, there were obtained 35 mg (10%) of 3,4-bis-(1- methyl-3-indolyl) -1H-pyrrole-2,5-dione in the form of a red solid of melting point >300° C.

The phenyl 1-methyl-3-indoleacetimidate hydrochloride used as the starting material was prepared as follows:

Hydrogen chloride was bubbled through a solution of 3 g (176 mmol) of 1-methylindole-3-acetonitrile and 8.28 g (88 mmol) of phenol in 70 ml of dry diethyl ether for 2 hours and the resulting solution was left to stand for 4 days. The solvent was removed under reduced pressure. The residual gum was triturated with diethyl ether to give 1.4 g (30%) of 1-methyl3-indoleacetimidate hydrochloride in the form of a purple solid of melting point 119° C.

Example 14

A solution of 222 mg (1 mmol) of 1-methylindole-3-glyoxylyl chloride in 25 ml of dichloromethane was added dropwise to a stirred solution of 138 mg (1 mmol) of isopropyl ethanimidate hydrochloride and 404 mg (4 mmol) of triethylamine in 25 ml of dry dichloromethane under a nitrogen atmosphere. After 18 hours, the mixture was washed twice with water, dried over sodium sulfate and evaporated under reduced pressure. The residue was dissolved in 25 ml of dry toluene under a nitrogen atmosphere and the solution obtained was treated with 112 mg (1 mmol) of potassium tert.butoxide. After stirring for 1 hour at room temperature, 380 mg (2 mmol) of p-toluenesulfonic acid were added and stirring was continued for an additional hour. The mixture was then poured into water and extracted three times with dichloromethane. The combined organic extracts were dried over sodium sulfate and evaporated to dryness. The residue was purified by flashy:-chromatography on silica gel using dichloromethane/ethyl acetate (9:1) for the elution to give 102mg (45%) of 3-(1-methyl-3-indolyl)-1H-pyrrole-2,5dione in the form of a yellow solid of melting point 229°–231° C.

Example 15

In a manner analogous to that described in Example 14, from 222 mg (1 mmol) of 1-methylindole-3-glyoxylyl chloride and 361 mg (1 mmol) of isopropyl stearimidate hydrochloride, there were obtained 289mg (64%) of 3-(1-hexadecyl)-4-(-1-methyl-3-indolyl) -1H-pyrrole-2,5-dione as a yellow solid of melting point 112°–114° C.

The isopropyl stearimidate hydrochloride used as the starting material was prepared as follows:

In a manner analogous to that described in Example 1, from stearonitrile there was obtained isopropyl stearimidate hydrochloride as a white solid of melting point 54°–55° C.

Example 16

A solution of 369 mg (1 mmol) of pentafluorophenyl 1-methylindole-3-glyoxylate in 20 ml of dichloromethane was added to a stirred solution of 266 mg (1 mmol) of isopropyl 1-methyl-3-indoleacetimidate hydrochloride and 404 mg (4 mmol) of triethylamine in 25 ml of dichloromethane. The solution obtained was heated to reflux under nitrogen for 18 hours, cooled and treated with 950 mg (5 mmol) of p-toluenesulfonic acid. After 1 hour, the solvent was removed under reduced pressure. The residue was purified by flash chromatography on silica gel using dichloromethane/ethyl acetate (8:1) for the elution to give 159mg (45%) of 3,4-bis-(1-methyl-3-indolyl)-1H-pyrrole-2,5-dione in the form of an orange colored solid of melting point >310° C.

The pentafluorophenyl 1-methylindole-3-glyoxylate used as the starting material was prepared as follows:

1.13 g (5.5 mol) of dicyclohexylcarbodiimide were added to a solution, cooled in ice, of 1 g (5 mmol) of 1-methylindole-3glyoxylic acid and 1.01 g (5 mmol) of pentafluorophenol in 50 ml of dry tetrahydrofuran. After stirring for 4 hours under a nitrogen atmosphere at 0° C., the mixture was allowed to warm to room temperature and left to stand for 60 hours. Then, 3 ml of glacial acetic acid were added and the mixture obtained was filtered. The filtrate was concentrated under reduced pressure. The residue was purified by flash chromatography on silica gel using dichloromethane for the elution to give 404 mg (22%) of pentafluorophenyl 1-methylindole-3-glyoxylate in the form of a pale yellow solid of melting point 168°–9° C.

Example 17

In a manner analogous to that described in Example 14, from 222 mg (1 mmol) of 1-methylindole-3-glyoxlyl chloride and 220 mg (1 mmol) of isopropyl cyclohexylacetimidate hydrochloride, there were obtained 109 mg (37%) of 3-cyclohexyl-4-(1-methyl-3-indolyl) -1H-pyrrole-2,5-dione in the form of a yellow solid of melting point 224°–225° C.

The isopropyl cyclohexylacetimidate hydrochloride used as the starting material was prepared as follows:

In a manner analogous to that described in Example 1, from cyclohexylacetonitrile, there was obtained isopropyl cyclohexylacetimidate hydrochloride in the form of a pale pink solid of melting point 108°–110° C.

Example 18

109 mg (1 mmol) of chlorotrimethylsilane were added to a stirred solution of 188 mg (1 mmol) of 1-methylindole-3-acetamide and 110 mg (1.1 mmol) of triethylamine in 25 ml of dry dichloromethane. After 0.5 hour at room temperature, an additional 202 mg (2 mmol) of triethylamine were added, followed by a solution of 222 mg (1 mmol) of 1-methylindole-3-glyoxylyl chloride in 25 ml of dry dichloromethane. After completion of the addition, the mixture obtained was stirred at room temper- ature for 18 hours. Then, 950 mg (5 mmol) of p-toluenesulfonic acid were added and stirring was continued for 1 hour. The solvent was evaporated under reduced pressure and the residue was purified by flash chromatography on silica gel using dichloromethane/ethyl acetate (8:1) for the elution to give 49 mg of (14%) 3,4-bis-(1-methyl-3-indolyl)-1H-pyrrole-2,5dione as a red solid of melting point 304°–307° C.

Example 19

A solution of 802 mg of pentafluorophenyl pyruvate in 20 ml of dichloromethane was added dropwise to a solution of 266 mg (1 mmol) of isopropyl 1-methyl-3-indoleacetimidate hydrochloride and 808 mg (8 mmol) of triethylamine in 20 ml of dichloromethane. After completion of the addition, the mixture was stirred at room temperature for 18 hours. Then, 1.9 g (10 mmol) of p-toluenesulfonic acid were added and stirring was continued for 1 hour. The solvent was removed under reduced pressure. The residue was purified by flash chromatography on silica gel using ethyl acetate/dichloromethane (1:8) for the elution to give 24 mg( 10% ) of 3-methyl-4-( 1 -methyl-3-indolyl)- 1H-pyrrole-2,5-dione in the form of a yellow solid of melting point 181° C.

The pentafluorophenyl pyruvate used as the starting material was prepared as follows:

736 mg (4 mmol) of pentafluorophenol and 825 mg (4 mmol) of dicyclohexylcarbodiimide were added to a stirred solution of 352 mg (4 mmol) of pyruvic acid in 10 ml of dichloromethane at 0° C. under nitrogen. The mixture obtained was diluted with 40 ml of dichloromethane and stirred at room temperature for 18 hours. The solvent was removed under reduced pressure. The residue was treated with 5 ml of cold ethyl acetate. The mixture was filtered and the filtrate was evaporated to dryness. The residue was purified by flash chromatography on silica gel using ethyl acetate/dichloromethane (1:8) for the elution to give 802 mg of pentafluorophenyl pyruvate.

Example 20

In a manner analogous to that described in Example 1, 333 mg (1 retool) of [8-(acetoxymethyl)-6,7,8,9-tetrahydropyrido[1,2-a]indol-10-yl]glyoxylyl chloride were treated with 266 mg (1 mmol) of isopopyl 1-methyl-3-indoleacetimidate hydrochloride in different solvents and at various temperatures to give 3-[8-(acetoxymethyl)-6,7,8,9-tetrahydropyrido[1,2-a]indol- 10-yl ]-4-( 1-methyl-3-indolyl)- 1H-pyrrole-2,5-dione. The results obtained are compiled in Table I:

TABLE I

| Solvent | Temperature | Yield |
| --- | --- | --- |
| Dichloromethane | 0° C. | 228 mg (49%) |
| Dichloromethane | 25° C. | 256 mg (55%) |
| Dichloromethane | 40° C. | 269 mg (58%) |
| Dimethylformamide | 25° C. | 195 mg (42%) |
| Ethyl acetate | 25° C. | 312 mg (67%) |
| Dimethoxyethane | 25° C. | 199 mg (43%) |
| Tetrahydrofuran | 25° C. | 219 mg (47%) |
| Acetonitrile | 25° C. | 162 mg (35%) |
| Dioxane | 25° C. | 10 mg (2%) |

TABLE I-continued

| Solvent | Temperature | Yield |
| --- | --- | --- |
| Toluene | 25° C. | 310 mg (67%) |
| tert-Butyl methyl ether | 25° C. | 157 mg (34%) |

Example 200

In a manner analogous to that described in Example 1, 333 mg (1 mmol) of [8-(acetoxymethyl)-6,7,8,9-tetrahydropyrido[1,2-a]indol- 10-yl]glyoxylyl chloride were reacted with 266 mg (1 mmol) of isopropyl 1-methyl-3-indoleacetamidate hydrochloride using toluene as the solvent and different bases to give 3-[8-(acetoxymethyl)-6,7,8,9-tetrahydropyrido-1,2-a]indol-10-yl]-4-( 1 -methyl-3-indolyl)- 1H-pyrrole-2,5-dione. The results are compiled in Table II.

TABLE II

| Base | Yield |
| --- | --- |
| Dimethylaminopyridine | 130 mg (28%) |
| Diisopropylethylamine | 177 mg (38%) |
| Pyridine | 87 mg (19%) |
| N-Ethylmorpholine | 130 mg (28%) |
| DABCO | 149 mg (32%) |

*DABCO = 1,4-diaminobicyclo[2,2,2]octane.

Example 22

A stirred solution of 2.43 g (10 mmol) of (S)-8-(acetoxymethyl)-6,7,8,9-tetrahydropyrido [1,2-a]indole (prepared as described in Example 2) in 15 ml of dichloromethane was treated at 0° C. with a solution of 1.27 g (10 mmol) of oxalyl chloride in 5 ml of dichloromethane. The solution was stirred for 15 minutes and then treated with 2.67 g (10 mmol) of isopropyl 1-methyl-3-indoleacetimidate hydrochloride (prepared as described in Example 1) followed by 10 ml of dichloromethane. The mixture obtained was treated with 5.05 g (10 mmol) of triethylamine, allowed to warm to room temperature and stirred for 2 hours. The mixture was then washed with water and the organic layer was dried over magnesium sulfite and evaporated to dryness. The residue was dissolved in 30 ml of pyridine, cooled in ice and treated dropwise with 2.10 g (10 mmol) of trifluoroacetic anhydride over 2-3 minutes. After 15 minutes, the solvent was evaporated in vacuo and the residue was partitioned between dichloromethane and 2M hydrochloric acid. The organic layer was washed with water and saturated sodium bicarbonate solution, dried over magnesium sulfite and evaporated. The residue was triturated with 30 ml of methanol and the solid was removed by filtration. The product was washed with methanol and dried to give 2.45 g (52%) of (S)-3-[8-(acetoxymethyl)-6,7,8,9-tetrahydro-pyrido [1,2-a]indol- 10-yl]-4(1-methyl-3-indolyl)-1H-pyrrole-2,5-dione in the form of a red solid of melting point 238°-241° C.

I claim:

1. A process for the preparation of substituted maleimides of the formula

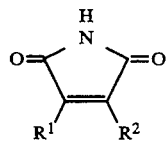

(I)

wherein $R^1$ is an optionally substituted bicyclic or tricyclic aromatic ring in which one or more carbon atoms have been replaced by one or more nitrogen atoms and $R^2$ is hydrogen, alkyl of a maximum of 8 carbon atoms, an optionally substituted monocyclic or bicyclic aromatic ring, or an optionally substituted monocyclic, bicyclic, or tricyclic aromatic ring in which one or more carbon atoms have been replaced by one or more nitrogen and/or sulfur atoms which comprises reacting an activated glyoxylate of the formula

(II)

wherein $R^1$ is as described above and X is a halogen atom, alkoxycarbonyloxy of a maximum of 8 carbon atoms in the alkoxy group, or pentafluorophenoxy, with an imidate of the formula

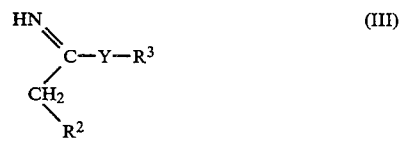

(III)

wherein $R^2$ is as described above, $R^3$ is alkyl of a maximum of 8 carbon atoms, an optionally substituted monocyclic, bicyclic or polycyclic aromatic ring, or trialkylsilyl wherein the alkyl group is of a maximum of 8 carbon atoms, and Y is oxygen or sulfur, in the presence of a base and, after treating a reaction product obtained in which $R^2$ is hydrogen or alkyl of a maximum of 8 carbon atoms, with a strong base, treating the resulting hydroxy-pyrrolinone of the formula

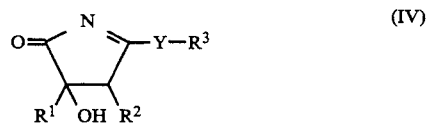

(IV)

wherein $R^1$, $R^2$, $R^3$ and Y are as described above, with a mineral acid or an organic acid or by treatment with acylating agent and a suitable base, and recovering the resulting of formula I.

2. A process according to claim 1, wherein in the activated glyoxylate of formula II $R^1$ is optionally substituted phenyl, naphthyl, thienyl, benzothiophenyl or indolyl.

3. A process according to claim 2, wherein $R^1$ is a 3-indolyl group of the formula

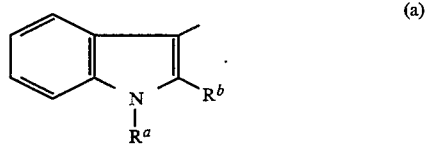

(a)

wherein $R^a$ is alkyl of a maximum of 8 carbon atoms, or alkanoyl and $R^b$ is hydrogen or alkyl of a maximum of 8 carbon atoms, or $R^a$ and $R^b$ taken together are a tetramethylene group optionally substituted by acetoxymethyl.

4. A process according to claim 3, wherein $R^a$ is methyl or acetyl and $R^b$ is hydrogen or methyl or $R^a$ and $R^b$ taken together are unsubstituted tetramethylene or tetramethylene substituted by acetoxymethyl.

5. A process according to claim 4, wherein in the activated glyoxylate of formula II X is a halogen atom.

6. A process according to claim 5, wherein in the imidate of formula III $R^2$ is indolyl or indolyl substituted by alkyl of a maximum of 8 carbon atoms.

7. A process according to claim 6, wherein in the imidate of formula III $R^3$ is a secondary alkyl of a maximum of 8 carbon atoms.

8. A process according to claim 7, wherein the reaction of an activated glyoxylate of formula II with an imidate of formula III is carried out in the presence of a tertiary amine or pyridine.

9. A process according to claim 8, wherein a reaction product obtained in which $R^2$ is hydrogen or alkyl of a maximum of 8 carbon atoms, is treated with an alkali metal alkoxide.

10. A process according to claim 9, wherein the steps are carried without separation.

* * * * *

UNITED STATES PATENT AND TRADEMARK OFFICE
CERTIFICATE OF CORRECTION

PATENT NO. : 5,399,712
DATED : March 21, 1995
INVENTOR(S) : Christopher Huw Hill It is certified that error appears in the above-indentified patent and that said Letters Patent is hereby corrected as shown below:

Claim 1, Column 12, lines 46-47: "or by treatment with acylating agent" should read --- or by treatment with an acylating agent --- .

Signed and Sealed this

Second Day of January, 1996

Attest:

BRUCE LEHMAN

Attesting Officer

Commissioner of Patents and Trademarks